(12) United States Patent
Wang et al.

(10) Patent No.: US 12,285,530 B2
(45) Date of Patent: Apr. 29, 2025

(54) MEDICAL MOISTURIZING EYE PATCH AND PREPARATION METHOD THEREOF

(71) Applicant: Zhende Medical Co., Ltd., Shaoxing (CN)

(72) Inventors: Jiao Wang, Shaoxing (CN); Jianguo Lu, Shaoxing (CN)

(73) Assignee: Zhende Medical Co., Ltd., Shaoxing (CN)

( * ) Notice: Subject to any disclaimer, the term of this patent is extended or adjusted under 35 U.S.C. 154(b) by 742 days.

(21) Appl. No.: 17/453,964

(22) Filed: Nov. 8, 2021

(65) Prior Publication Data

US 2022/0054428 A1 Feb. 24, 2022

Related U.S. Application Data

(63) Continuation of application No. PCT/CN2020/119564, filed on Sep. 30, 2020.

(30) Foreign Application Priority Data

Jul. 16, 2020 (CN) .......................... 202010686635.7

(51) Int. Cl.
*A61K 9/70* (2006.01)
*A61K 9/00* (2006.01)
*A61K 31/717* (2006.01)
*A61K 45/06* (2006.01)

(52) U.S. Cl.
CPC .......... *A61K 9/7092* (2013.01); *A61K 9/0014* (2013.01); *A61K 31/717* (2013.01); *A61K 45/06* (2013.01)

(58) Field of Classification Search
None
See application file for complete search history.

(56) References Cited

FOREIGN PATENT DOCUMENTS

| CN | 101559032 A | 10/2009 |
|---|---|---|
| CN | 201356709 Y | 12/2009 |
| CN | 102784071 A | 11/2012 |
| CN | 205007294 U | 2/2016 |
| CN | 105476867 A | 4/2016 |
| CN | 206334009 U | 7/2017 |
| CN | 108403757 A | 8/2018 |
| CN | 111643375 A | 9/2020 |

OTHER PUBLICATIONS

"Chinese Application No. 202010686635.7, First Office Action dated Feb. 23, 2021", (Feb. 23, 2021), 8 pgs.
"Chinese Application No. 202010686635.7, Search Report dated Feb. 18, 2021", (Feb. 18, 2021), 2 pgs.
"Chinese Application No. 202010686635.7, Second Office Action dated Jul. 8, 2021", (Jul. 8, 2021), 7 pgs.

*Primary Examiner* — David J Blanchard
*Assistant Examiner* — Sarah J Chickos
(74) *Attorney, Agent, or Firm* — Schwegman Lundberg & Woessner, P.A.

(57) ABSTRACT

The disclosure relates to a medical moisturizing eye patch with excellent biocompatibility and lasting moisture retention and a preparation method thereof, in which firstly, the standing cultured bacterial cellulose film is purified and bleached; then, the bleached bacterial cellulose wet film is composited with a moisturizing agent; then, a mechanical pressing is made to be with a proper liquid content; and finally, a cutting is made to obtain the eye patch with a proper size, which has excellent biocompatibility, high water holding capacity, high purity, high wet strength and excellent flexibility, excellent water absorption and water locking effect, improved skin moisture content, good air permeability, antibacterial function and no side-effect. The preparation method in the disclosure is simple and easy to realize; and the eye patch can be directly applied after peeling away the backing layer in use.

7 Claims, 1 Drawing Sheet

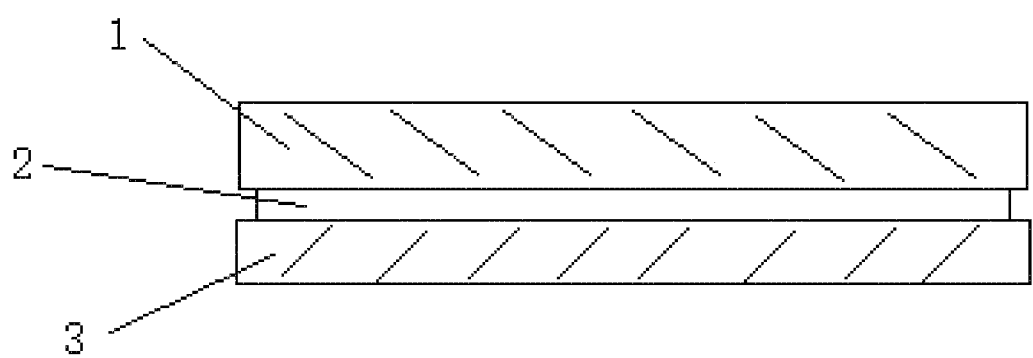

MEDICAL MOISTURIZING EYE PATCH AND PREPARATION METHOD THEREOF

CROSS-REFERENCE TO RELATED APPLICATIONS

This application is a continuation of International Application No. PCT/CN2020/119564 filed 30 Sep. 2020, which claims the benefit of priority to Chinese Application No. CN202010686635.7, filed 16 Jul. 2020, the benefit of priority of each of which is claimed herein and which applications are hereby incorporated by reference herein in their entirety.

TECHNICAL FIELD

The disclosure belongs to a technical field of eye patches, and particularly relates to a medical moisturizing eye patch with excellent biocompatibility and lasting moisturizing and a preparation method thereof.

BACKGROUND ART

An eye patch is a film that can be applied to an orbit, with three main functions: first, preventing ocular lesions; second, effectively relieving eye fatigue and combating vision decline; and third, moistening eyes and relieving dryness of eyes.

With increased quality of people's life, pursuit of beautiful things has increasingly grown in popularity, and eye patches with cosmetic effect are becoming more and more popular. As age increases, subcutaneous fat shrinks gradually, skin becomes thinner, and collagen that provides skin water retention and elasticity also slowly lose, which results in degrading of the skin elasticity, sagging of ocular skin, and also appearance of lacrimal grooves on an inner side of lower eyelid. In addition, when exposed to ultraviolet rays in outdoor sports or staying in an air-conditioning room, there will be dryness or even peeling around the eyes. The dryness around the eyes is also prone to fine lines. Therefore, there has been a strong demand for eye patches with anti-wrinkle effect.

For example, an anti-wrinkle elastic eye patch is disclosed in a Chinese patent (publication No. CN101559032A), which is composed of a nano 24K gold-platinum sheet and a cosmetic substance coated on the gold-platinum sheet.

The cosmetic substance include Carbopoi resin, alkanolamine, hydroxyethyl cellulose, sodium hyaluronate, allantoin, witch hazel distillate, Vb3, glycerin, plant extract and purified water. The plant extract contains EYELISS polypeptides, PHYTOLIGHT compound extract and GULCKLIFT xanthan gum polymer, and with careful screening and formulating of cosmetic substances and with nano gold-platinum sheet added, it can effectively provide an anti-oxidation and anti-aging effect. Although the eye patch has some effect of delaying skin aging, its components are not natural substances, and its applicable people are limited and its cost is high.

For example, Chinese patent (application No. CN201810274650.3) discloses an easy-to-bond eye patch, which belongs to a technical field of biomaterial. The easy-to-bond eye patch is made by following steps: weighting modified bacterial cellulose, essential oil mixture, mixed enzyme solution, carbomer, glycylglycine, emulsifier and Chinese herb extract; mixing the carbomer with the Chinese herb extract; adjusting pH of a mixture of the carbomer with the Chinese herb extract to 6.8-7.4 to obtain pretreated Chinese medicine extract; mixing the modified bacterial cellulose with the pretreated Chinese herb extract; adding the essential oil, the mixed enzyme solution, the glycylglycine and the emulsifier in turn and stirring and mixing to obtain blank liquid; transferring the blank liquid into a mold; freezing at 20~12° C. for 30 ~40 min, and thawing at room temperature for 40~50 min; repeating the freezing and thawing for 5~6 times, and then demoulding. Moisturizing effect has not been studied for the eye patch, and its composition and preparation method are complex.

For example, Chinese patent (application No. CN201210248774.7) discloses a moisturizing eye mask made of bacterial cellulose, and a preparation method of the moisturizing eye mask made of the bacterial cellulose includes following steps: inoculating 1-2 rings of activated slant seed *acetobacter* xylinum into a culture medium and shaking culturing to obtain a seed solution; then inoculating the seed solution into the culture medium, fully shaking the seed solution and the culture medium to obtain evenly mixed bacterial solution, then standing culturing to obtain a bacterial cellulose film floated on a liquid surface, taking the generated bacterial cellulose film and washing it with water to remove the culture medium and impurities on the film surface, then immersing the film in an alkaline solution to remove bacteria and residual culture medium in the film, finally washing it with distilled water and measuring pH of the film until the film with pH of 7.0-7.2 is obtained; then cutting a bacterial cellulose wet film to be the eye mask. According to the method, the standing cultured bacterial cellulose film is purified and then directly cut to be the eye patch, and the prepared eye patch does not contain moisturizing measures, thus with poor moisturizing effect for the eye patch.

SUMMARY

In order to solve above problems, the disclosure provides a medical moisturizing eye patch with excellent biocompatibility and lasting moisturizing and a preparation method thereof, which provide a simple preparation method, a lasting moisturizing effect, and antibacterial and anti-inflammatory effects.

In order to achieve the above object, the disclosure adopts following technical schemes.

A medical moisturizing eye patch is provided, which is composed of a protective layer, a gel layer and a backing layer. Raw materials of the gel layer include a component A with excellent biocompatibility and a component B with a moisturizing ingredient. A liquid content of the medical moisturizing eye patch is 90-98%, with a weight per square meter of 800-1500 $g/m^2$.

Preferably, the protective layer is made of a silica gel film. The backing layer is made of non-woven fabric.

Preferably, the component A is a bacterial cellulose wet film subjected to pretreating. The component B includes following raw materials in percentage by mass: 0.5-5% of glycerol, 0.05-5% of sodium hyaluronate with a molecular weight higher than 500,000, 0.05-5% of sodium hyaluronate with a molecular weight of 1,000-500,000, 0.05-0.3% of Nipagin ester and balance water. The manufacturer of the bacterial cellulose wet film is Zhende Medical Co., Ltd. and the model number is ZD-BC-5A. Preferably, the molecular weight of sodium hyaluronate with molecular weight of 1,000-500,000 is selected from 200,000-400,000, and the molecular weight of sodium hyaluronate with molecular weight higher than 500,000 is selected from 4,000,000-5,000,000.

Preferably, a weight ratio of the component A to the component B is 1:1-1:5.

Preferably, the pretreating includes: stirring the bacterial cellulose wet film in a 0.5-1.5%, by mass, sodium hydroxide solution at 80-100° C. for 1-2 h, washing it to neutrality, then stirring with a 0.5-3%, by mass, hydrogen peroxide solution at normal temperature for 4-6 h, and then washing until the residual hydrogen peroxide is less than 0.5 mg/L.

A preparation method of the medical moisturizing eye patch includes following steps:

1) preparing a component A, including: stirring a bacterial cellulose wet film in a sodium hydroxide solution for 1-2 h, washing it to neutrality, stirring with a hydrogen peroxide solution at normal temperature for 4-6 h, and washing until the residual hydrogen peroxide is less than 0.5 mg/L, so as to obtain the component A;
2) preparing a component B, including: dissolving glycerol and Nipagin ester uniformly in water bath by heating and stirring; adding sodium hyaluronate with molecular weight higher than 500,000 and sodium hyaluronate with molecular weight of 1,000-500,000, stirring at normal temperature for 24 h, adding water to make up 100%, and stirring for 10-20 min, so as to obtain the component B;
3) preparing a gel layer, including: compositing the component A obtained in the step 1) and the component B obtained in the step 2) at a weight ratio of 1:1-1:5, and stirring for 2-4 hours at normal temperature to obtain the gel layer;
4) preparing the medical moisturizing eye patch, including: covering one side of the gel layer obtained in step 3) with a protective layer and the other side with a silica gel film, mechanically pressing the gel layer to be with a water content of 90-98% and a weight per square meter of 800-1500 g/m$^2$, and cutting the gel layer into the eye patch with an appropriate size using a cutting die.

Preferably, in step 1), the sodium hydroxide solution is of 0.5-1.5% by mass, temperature of the sodium hydroxide solution is 80-100° C., and the hydrogen peroxide solution is of 0.5-3% by mass.

Preferably, in step 2), the glycerin and Nipagin ester are taken with 10%-20% water added, and heated to 70-80° C. in water bath and stirred evenly; then the dissolved glycerol and Nipagin ester, the sodium hyaluronate with molecular weight higher than 500,000 and the sodium hyaluronate with molecular weight of 1,000-500,000 are sequentially put into 60-70% water and stirred at normal temperature for 24 hours; finally, the balance water is added to 100%, and stirred for 10-20 min at normal temperature.

In this disclosure, firstly, the standing cultured bacterial cellulose film is purified and bleached; then, the bleached bacterial cellulose wet film is composited with a moisturizing agent; then, a mechanical pressing is made to be with a proper liquid content and a weight per square meter; and finally, a cutting is made to obtain the eye patch with a proper size.

The gel layer is composed of the bacterial cellulose wet film containing a moisturizing ingredient. The bacterial cellulose wet film is composed of extracellular cellulose produced by microorganisms, with a chemical structure of a straight chain macromolecule formed by connecting D-glucoside with β-1,4-glucosidic bonds, which presents physicochemical properties such as excellent biocompatibility, high water holding capacity, high purity, high wet strength and excellent flexibility.

Hyaluronic acid (HA) is a linear macromolecular acidic mucopolysaccharide formed by alternately connecting D-glucuronic acid and N-acetylglucosamine in a disaccharide unit. Commercial HA is generally its sodium salt, namely sodium hyaluronate. Sodium hyaluronate exists widely in bodies, which is high in amount in joint cavities, skins, vitreous bodies, cartilages, umbilical cords and cock crowns or the like. The sodium hyaluronate has good moisturizing performance, and sodium hyaluronate with a high molecular weight achieves a purpose of moisturizing by evaporating water inside the skin; sodium hyaluronate with a low molecular weight can increase skin moisture content, but with no effect of preventing moisture loss. Therefore, in order to achieve better moisturizing effect, the sodium hyaluronate with the high molecular weight and the sodium hyaluronate with the low molecular weight can be combined.

In the disclosure, the hyaluronic acid is selected with the high low molecular weight or the low molecular weight, and the sodium hyaluronate with the high molecular weight cannot easily enter a three-dimensional network structure of the bacterial cellulose wet film, but form a protective film on a outer layer of the bacterial cellulose wet film, and when a product is externally applied to eyes, it will form a film on a skin surface of the eyes and cannot be absorbed by the skin; and the sodium hyaluronate with the low molecular weight can penetrate into the skin to lock moisture.

Glycerol is a polyol moisturizing agent, and hydroxyl groups in its molecular structure can form hydrogen bonds with water molecules, which functions well in absorbing and locking water, and improves the moisture content of the skin. Nipagin ester provides Antibacterial and antiseptic functions.

The protective layer is composed of a silica gel film which is vapour permeable water resistant, thus increasing air permeability of the product.

The backing layer is composed of non-woven fabric.

The disclosure presents beneficial effects as follows: firstly, the standing cultured bacterial cellulose film is purified and bleached; then, the bleached bacterial cellulose wet film is composited with a moisturizing agent; then, a mechanical pressing is made to be with a proper liquid content and weight per square meter; and finally, a cutting is made to obtain the eye patch with a proper size, which has excellent biocompatibility, high water holding capacity, high purity, high wet strength and excellent flexibility, excellent water absorption and water locking effect, improved skin moisture content, good air permeability, antibacterial function and no side-effect. The preparation method in the disclosure is simple and easy to realize; and the eye patch can be directly applied after peeling away the backing layer in use.

BRIEF DESCRIPTION OF THE DRAWINGS

FIG. 1 is a cross-sectional view of Embodiment 1 of the present disclosure.

In the figure, 1. Protective Layer; 2. Gel Layer; 3. Backing Layer.

DETAILED DESCRIPTION

In order to further understand the present disclosure, the preferred embodiments of the present disclosure will be described below with reference to specific implementations, but it should be understood that these descriptions are only for further explaining features and advantages of the present disclosure, but not for limiting claims of the present disclosure.

Referring to FIG. 1, a medical moisturizing eye patch of the present disclosure is composed of a protective layer 1, a gel layer 2 and a backing layer 3. The protective layer 1 is made of a silica gel film which is vapour permeable water resistant, which can increase air permeability of the product. The backing layer 3 is made of non-woven fabric, and its raw materials come from wide sources and are simple and easy to obtain. The gel layer 2 includes a component A with excellent biocompatibility composited with a component B with a moisturizing ingredient. A liquid content of the medical moisturizing eye patch is 90-98%, with a weight per square meter of 800-1500 $g/m^2$.

Embodiment 1

A preparation method of the medical moisturizing eye patch provided in this embodiment includes following steps:
1) preparing a component A, including: stirring a bacterial cellulose wet film in in a 0.5%, by mass, sodium hydroxide solution at 80° C. for 1 h, washing it to neutrality, stirring with a 0.5%, by mass, hydrogen peroxide solution at normal temperature for 4 h, and washing until the residual hydrogen peroxide is less than 0.5 mg/L, so as to obtain the component A;
2) preparing a component B, including: taking the glycerin and nipagin ester 10% water added, and heating to 70° C. in water bath and stirring and dissolving evenly; then sequentially putting the dissolved glycerol and Nipagin ester, the sodium hyaluronate with molecular weight higher than 500,000 and the sodium hyaluronate with molecular weight of 1,000-500,000 into 60% water and stirred at normal temperature for 24 hours; finally, adding the balance water to 100%, and stirring for 10 min at normal temperature, in which the component B includes following raw materials in percentage by mass: 0.5% of glycerol, 0.05% of sodium hyaluronate with a molecular weight higher than 500,000, 0.05% of sodium hyaluronate with a molecular weight of 1,000-500,000, 0.05% of Nipagin ester and balance water;
3) preparing a gel layer, including: compositing the component A obtained in the step 1) and the component B obtained in the step 2) at a weight ratio of 1:1, and stirring for 2 hours at normal temperature to obtain the gel layer;
4) preparing the medical moisturizing eye patch, including: covering one side of the gel layer obtained in step 3) with a protective layer and the other side with a silica gel film, mechanically pressing the gel layer to be with a water content of 90-98% and a weight per square meter of 800 $g/m^2$, and cutting the gel layer into the eye patch with an appropriate size using a cutting die.

Embodiment 2

A preparation method of the medical moisturizing eye patch provided in this embodiment includes following steps:
1) preparing a component A, including: stirring a bacterial cellulose wet film in in a 1%, by mass, sodium hydroxide solution at 90° C. for 1.5 h, washing it to neutrality, stirring with a 2%, by mass, hydrogen peroxide solution at normal temperature for 5 h, and washing until the residual hydrogen peroxide is less than 0.5 mg/L, so as to obtain the component A;
2) preparing a component B, including: taking the glycerin and Nipagin ester 15% water added, and heating to 75° C. in water bath and stirring and dissolving evenly; then sequentially putting the dissolved glycerol and Nipagin ester, the sodium hyaluronate with molecular weight higher than 500,000 and the sodium hyaluronate with molecular weight of 1,000-500,000 into 65% water and stirred at normal temperature for 24 hours; finally, adding the balance water to 100%, and stirring for 15 min at normal temperature, in which the component B includes following raw materials in percentage by mass: 3% of glycerol, 2.5% of sodium hyaluronate with a molecular weight higher than 500,000, 3% of sodium hyaluronate with a molecular weight of 1,000-500,000, 0.3% of Nipagin ester and balance water;
3) preparing a gel layer, including: compositing the component A obtained in the step 1) and the component B obtained in the step 2) at a weight ratio of 1:2, and stirring for 3 hours at normal temperature to obtain the gel layer;
4) preparing the medical moisturizing eye patch, including: covering one side of the gel layer obtained in step 3) with a protective layer and the other side with a silica gel film, mechanically pressing the gel layer to be with a water content of 90-98% and a weight per square meter of 1200 $g/m^2$, and cutting the gel layer into the eye patch with an appropriate size using a cutting die.

Embodiment 3

A preparation method of the medical moisturizing eye patch provided in this embodiment includes following steps:
1) preparing a component A, including: stirring a bacterial cellulose wet film in in a 1.5%, by mass, sodium hydroxide solution at 100° C. for 2 h, washing it to neutrality, stirring with a 3%, by mass, hydrogen peroxide solution at normal temperature for 6 h, and washing until the residual hydrogen peroxide is less than 0.5 mg/L, so as to obtain the component A;
2) preparing a component B, including: taking the glycerin and nipagin ester 20% water added, and heating to 80° C. in water bath and stirring evenly; then sequentially putting the dissolved glycerol and Nipagin ester, the sodium hyaluronate with molecular weight higher than 500,000 and the sodium hyaluronate with molecular weight of 1,000-500,000 into 70% water and stirred at normal temperature for 24 hours; finally, adding the balance water to 100%, and stirring for 20 min at normal temperature, in which the component B includes following raw materials in percentage by mass: 5% of glycerol, 5% of sodium hyaluronate with a molecular weight higher than 500,000, 5% of sodium hyaluronate with a molecular weight of 1,000-500,000, 0.3% of Nipagin ester and balance water;
3) preparing a gel layer, including: compositing the component A obtained in the step 1) and the component B obtained in the step 2) at a weight ratio of 1:5, and stirring for 4 hours at normal temperature to obtain the gel layer;
4) preparing the medical moisturizing eye patch, including: covering one side of the gel layer obtained in step 3) with a protective layer and the other side with a silica gel film, mechanically pressing the gel layer to be with a water content of 90-98% and a weight per square meter of 1500 $g/m^2$, and cutting the gel layer into the eye patch with an appropriate size using a cutting die.

In Comparative Example 1, the eye patch is prepared only using the bacterial cellulose film, with a same liquid content, weight per square meter and size as those in Embodiment 1.

Liquid holdups of the eye patches prepared in Embodiments 1 to 3 are tested at 37±1° C. after 0, 1, 2, 4, 8, 16 and 24 hours, and results are shown in Table 1.

TABLE 1

| Test results | | | | | | | |
|---|---|---|---|---|---|---|---|
| Liquid Holdup | Test Time/hour (h) | | | | | | |
| (%) | 0 h | 1 h | 2 h | 4 h | 8 h | 16 h | 24 h |
| Embodiment 1 | 94.2 | 88.4 | 81.6 | 73.4 | 63.3 | 45.1 | 35.2 |
| Embodiment 2 | 93.7 | 89.6 | 80.9 | 71.2 | 60.7 | 49.7 | 38.9 |
| Embodiment 3 | 93.8 | 90.9 | 86.3 | 76.8 | 69.5 | 55.3 | 48.6 |
| Comparative Example 1 | 94.6 | 72.7 | 60.6 | 45.3 | 33.8 | 10.1 | 4.2 |

It can be seen from Table 1 that the moisturizing effect of the medical moisturizing eye patch prepared by the present disclosure is far superior to that of the eye patch of Comparative Example 1, and the gel layer is composed of the bacterial cellulose wet film containing a moisturizing ingredient, and the bacterial cellulose wet film presents physicochemical properties such as excellent biocompatibility, high water holding capacity, high purity, high wet strength and excellent flexibility. The sodium hyaluronate has good moisturizing performance, and the sodium hyaluronate with the high molecular weight achieves a purpose of moisturizing by evaporating water inside the skin; the sodium hyaluronate with the low molecular weight can increase skin moisture content, but with no effect of preventing moisture loss. Therefore, in order to achieve better moisturizing effect, the sodium hyaluronate with the high molecular weight and the sodium hyaluronate with the low molecular weight can be combined. It can be seen from Table 1 that the liquid holdup of the eye patch made of the bacterial cellulose wet film after 0, 1, 2, 4, 8, 16 and 24 hours indicates that the moisture retention rate is very poor.

In the disclosure, the hyaluronic acid is selected with the high low molecular weight or the low molecular weight, and the sodium hyaluronate with the high molecular weight cannot easily enter a three-dimensional network structure of the bacterial cellulose wet film, but form a protective film on a outer layer of the bacterial cellulose wet film, and when a product is externally applied to eyes, it will form a film on a skin surface of the eyes and cannot be absorbed by the skin; and the sodium hyaluronate with the low molecular weight can penetrate into the skin to lock moisture.

The above description of the disclosed embodiments enables those skilled in the art to realize or use this disclosure. Various modifications to these embodiments will be obvious to those skilled in the art, and the general principles defined herein can be implemented in other embodiments without departing from the spirit or scope of this disclosure. Therefore, the disclosure will not be limited to the embodiments illustrated herein, but should conform to the widest scope consistent with the principles and novel features disclosed herein.

What is claimed is:

1. A preparation method of a medical moisturizing eye patch, the medical moisturizing eye patch is composed of a protective layer, a gel layer and a backing layer, wherein the gel layer comprises a component A with excellent biocompatibility and a component B with a moisturizing ingredient, and a liquid content of the medical moisturizing eye patch is 90-98% wgt/wgt, with a weight per square meter of 800-1500 g/m$^2$;

the preparation method comprising following steps:
1) preparing a component A, comprising: stirring a bacterial cellulose wet film in a sodium hydroxide solution for 1-2 h, washing it to a neutral pH, stirring with a hydrogen peroxide solution at ambient temperature for 4-6 h, and washing until the residual hydrogen peroxide is less than 0.5 mg/L, so as to obtain the component A;
2) preparing a component B, comprising: dissolving glycerol and paraben ester uniformly in water bath by heating and stirring; adding sodium hyaluronate with molecular weight higher than 500,000 and sodium hyaluronate with molecular weight of 1,000-500,000, stirring at ambient temperature for 24 h, adding water to make up 100% wgt/wgt, and stirring for 10-20 min, so as to obtain the component B;
3) preparing a gel layer, comprising: compositing the component A obtained in the step 1) and the component B obtained in the step 2) at a weight ratio of 1:1-1:5, and stirring for 2-4 hours at ambient temperature to obtain the gel layer;
4). preparing the medical moisturizing eye patch, comprising: covering one side of the gel layer obtained in step 3) with a protective layer and the other side with a silica gel film, mechanically pressing the gel layer to be with a water content of 90-98% wgt/wgt and a weight per square meter of 800-1500 g/m$^2$, and cutting the gel layer into the eye patch with an appropriate size by using a cutting die.

2. The preparation method of the medical moisturizing eye patch according to claim 1, wherein the protective layer is made of a silica gel film, and the backing layer is made of non-woven fabric.

3. The preparation method of the medical moisturizing eye patch according to claim 1, wherein the component A is a bacterial cellulose wet film subjected to pretreating, the component B comprises following raw materials in percentage by mass: 0.5-5% wgt/wgt of glycerol, 0.05-5% wgt/wgt of sodium hyaluronate with a molecular weight higher than 500,000, 0.05-5% wgt/wgt of sodium hyaluronate with a molecular weight of 1,000-500,000, 0.05-0.3% wgt/wgt of paraben ester and balance water.

4. The preparation method of the medical moisturizing eye patch according to claim 1, wherein a weight ratio of the component A to the component B is 1:1-1:5.

5. The preparation method of the medical moisturizing eye patch according to claim 3, wherein the pretreating comprises: stirring the bacterial cellulose wet film in a 0.5-1.5% wgt/wgt, by mass, sodium hydroxide solution at 80-100° C. for 1-2 h, washing it to a neutral pH, then stirring with a 0.5-3% wgt/wgt, by mass, hydrogen peroxide solution at ambient temperature for 4-6 h, and then washing until the residual hydrogen peroxide is less than 0.5 mg/L.

6. The preparation method of the medical moisturizing eye patch according to claim 1, wherein in step 1), the sodium hydroxide solution is of 0.5-1.5% wgt/wgt by mass, temperature of the sodium hydroxide solution is 80-100° C., and the hydrogen peroxide solution is of 0.5-3% wgt/wgt by mass.

7. The preparation method of the medical moisturizing eye patch according to claim 1, wherein in step 2), the glycerin and paraben ester are taken with 10% wgt/wgt-20% wgt/wgt water added, and heated to 70-80° C. in water bath, and stirred and dissolved evenly; then the dissolved glycerol and paraben ester, the sodium hyaluronate with molecular weight higher than 500,000 and the sodium hyaluronate with molecular weight of 1,000-500,000 are sequentially put into 60-70% wgt/wgt water and stirred at ambient temperature for 24 hours; finally, the balance water is added to 100% wgt/wgt, and stirred for 10-20 min at ambient temperature.

* * * * *